United States Patent [19]

Meurer et al.

[11] Patent Number: 5,756,860
[45] Date of Patent: May 26, 1998

[54] CRYSTALLINE ADDUCT OF BISPHENOL A AND BISPHENOL TMC

[75] Inventors: Kurt-Peter Meurer, Leverkusen, Germany; Tony Van Osselaer, Belsele, Belgium; Claus Wulff; Jürgen Hinz, both of Krefeld, Germany

[73] Assignee: Bayer Aktiengesellschaft, Leverkusen, Germany

[21] Appl. No.: 691,390

[22] Filed: Aug. 2, 1996

[30] Foreign Application Priority Data

Aug. 14, 1995 [DE] Germany ............ 195 29 857.8

[51] Int. Cl.⁶ .................................. C07C 37/84
[52] U.S. Cl. .................. 568/724; 568/722; 568/744
[58] Field of Search ..................... 568/722, 724, 568/744

[56] References Cited

U.S. PATENT DOCUMENTS

| 4,034,039 | 7/1977 | Sun. | |
|---|---|---|---|
| 4,912,263 | 3/1990 | Rudolph et al. | |
| 5,336,812 | 8/1994 | Salek et al. | 568/721 |
| 5,368,827 | 11/1994 | Moriya et al. | 422/245.1 |

FOREIGN PATENT DOCUMENTS

| 1 168 445 | 5/1960 | Germany. |
| 27 19 997 | 12/1977 | Germany. |
| 3727641 | 3/1989 | Germany. |

*Primary Examiner*—Gary Geist
*Assistant Examiner*—Sreeni Padmanabhan
*Attorney, Agent, or Firm*—Connolly and Hutz

[57] ABSTRACT

The invention relates to the preparation of a transparent crystalline adduct consisting of bisphenol A (75 parts) and bisphenol TMC (25 parts), which has a melting point of 144° C. which is below the melting points of the pure starting compounds bisphenol A (157° C.) and bisphenol TMC (208° C.).

2 Claims, No Drawings

CRYSTALLINE ADDUCT OF BISPHENOL A AND BISPHENOL TMC

The invention relates to the preparation of a transparent, crystalline adduct consisting of bisphenol A (75 parts) and bisphenol TMC (1,1-bis-(4-hydroxyphenyl)-3,3,5-trimethylcyclohexane) (25 parts) which has a melting point of 144° C. which is below the melting points of the pure starting components bisphenol A (157° C.) and bisphenol TMC (208° C.).

Technical, energetic and processing advantages are produced by the use of this type of crystalline adduct during the preparation of transparent and thermally stable polymers which are resistant to high temperature, such as polycarbonates.

Bisphenol A (BPA) is prepared by reacting phenol and acetone under acid conditions in the presence of optionally modified ion exchange resins (e.g. DE-A 3 727 641, corresponding to US-A 4,912,263).

Isolation is performed essentially via a graduated crystallisation procedure for bisphenol A/phenol adducts followed by filtration and removal of excess phenol. Bisphenol A prepared in this way is suitable, without any further purification, as a monomer for preparing highly transparent polymers such as, for instance, polycarbonates.

Bisphenol TMC is prepared by reacting 3,3,5-trimethylcyclohexanone and is used as a mixture with bisphenol A as an additional component for preparing transparent polycarbonates which are resistant to high temperature.

It has now been found that a mixture of 75 parts of high purity bisphenol A and 25 parts of high purity bisphenol TMC form a crystalline adduct from the melt, which has a sharp melting point at 144° C.

This melting point is below the melting point of bisphenol A (157° C.) and well below that of bisphenol TMC (208° C.).

The invention provides a crystalline adduct consisting of 75 parts by wt. of bisphenol A and 25 parts by wt. of bisphenol TMC with a melting point of 144° C., characterised in that a mixture of 90 to 60 parts by wt. of bisphenol A and 10 to 40 parts by wt. of bisphenol TMC is heated to a temperature of 150 to 160° C. and then cooled to a temperature <140° C.

The adduct prepared in accordance with the invention can be used to prepare high purity, transparent polymers which are resistant to high temperature such as, for instance, specific types of polycarbonate.

This adduct is used, for instance, to prepare high purity, transparent and thermally stable melts from bisphenol A and bisphenol TMC at temperatures <200° C. and can be stored as raw material and processed at this temperature.

The adduct prepared in accordance with the invention can be used to prepare high purity bisphenol TMC. This can be achieved by distillation and/or by crystallisation.

Mixed crystals of bisphenol A and phenol (60 parts of BPA: 40 parts of phenol) are known and are used as a process purification step in the process for preparing bisphenol A.

EXAMPLE 75 parts of bisphenol A and 25 parts of bisphenol TMC were mixed, melted at 160° C. and then allowed to solidify again. The melting point of the mixture was found to be 144° C.

DSC measurements were performed on mixtures of bisphenol A and bisphenol TMC (Table 1). A clear, sharp melting point was determined at 144° C.

TABLE 1

| GC analysis p,p-BPA | BP-TMC | DSC analysis | Melting range | |
|---|---|---|---|---|
| % | % | °C. | °C. | °C. |
| 0.00 | 100 | 205.9 | 203 | 210 |
| 5.00 | 95.0 | 202.4 | 182 | 206 |
| 10.0 | 90.0 | 198.0 | 170 | 205 |
| 15.0 | 85.0 | 196.3 | 140 | 202 |
| 20.0 | 80.0 | 191.7 | 155 | 200 |
| 25.0 | 75.0 | 188.5 | 150 | 198 |
| 30.0 | 70.0 | 184.5 | 145 | 193 |
| 35.0 | 65.0 | 181.5 | 135 | 195 |
| 40.0 | 60.0 | 177.2 | 150 | 195 |
| 45.0 | 55.0 | 173.2 | 133 | 183 |
| 50.0 | 50.0 | 169.3 | 130 | 180 |
| 55.0 | 45.0 | 159.3 | 128 | 180 |
| 60.0 | 40.0 | 141.6 | 115 | 170 |
| 65.0 | 35.0 | 142.8 | 115 | 165 |
| 70.0 | 30.0 | 142.4 | 115 | 165 |
| 75.0 | 25.0 | 144.4 | 115 | 165 |
| 80.0 | 20.0 | 140.2 | 120 | 155 |
| 85.0 | 15.0 | 145.5 | 125 | 155 |
| 90.0 | 10.0 | 152.3 | 125 | 160 |
| 95.0 | 5.0 | 154.8 | 130 | 165 |
| 100 | 0.00 | 157.1 | 145 | 165 |

What is claimed is:

1. A process for preparing a crystalline adduct of 75 parts by wt. of bisphenol A and 25 parts by wt. of bisphenol TMC with a melting point of 144° C., characterised in that a mixture of 90 to 60 parts by wt. of bisphenol A and 10 to 40 parts by wt. of bisphenol TMC is heated to a temperature of 150° to 160° C. and then cooled to a temperature <140° C.

2. A crystalline adduct of 75 parts by wt. of bisphenol A and 25 parts by wt. of bisphenol TMC with a melting pint of 144° C., prepared in accordance with claim 1.

* * * * *